United States Patent
Wagner et al.

(10) Patent No.: US 6,780,808 B2
(45) Date of Patent: Aug. 24, 2004

(54) ENHANCED SOLUBILITY OF MAGNESIUM HALIDES AND CATALYSTS AND POLYMERIZATION PROCESS USING SAME

(75) Inventors: Burkhard Eric Wagner, Highland Park, NJ (US); Robert James Jorgensen, Belle Mead, NJ (US); Cynthia Anne Hepburn, Edison, NJ (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 10/196,704

(22) Filed: Jul. 15, 2002

(65) Prior Publication Data

US 2004/0009869 A1 Jan. 15, 2004

(51) Int. Cl.$^7$ ............... B01J 31/00; B01J 37/00; C08F 4/02; C08F 4/60
(52) U.S. Cl. ............... 502/103
(58) Field of Search ............... 502/103

(56) References Cited

U.S. PATENT DOCUMENTS

| | | | |
|---|---|---|---|
| 3,989,881 A | 11/1976 | Yamaguchi et al. | |
| 4,158,642 A | * 6/1979 | Langer, Jr. ............... | 502/121 |
| 4,302,566 A | 11/1981 | Karol et al. | |
| 4,329,253 A | 5/1982 | Goodall et al. | |
| 4,330,649 A | 5/1982 | Kioka et al. | |
| 4,379,758 A | * 4/1983 | Wagner et al. ............... | 502/104 |
| 4,393,182 A | 7/1983 | Goodall et al. | |
| 4,414,132 A | 11/1983 | Goodall et al. | |
| 4,482,687 A | 11/1984 | Noshay et al. | |
| 4,540,679 A | 9/1985 | Arzoumanidis et al. | |
| 4,612,299 A | 9/1986 | Arzoumanidis et al. | |
| 4,684,703 A | 8/1987 | Wagner et al. | |
| 4,728,705 A | 3/1988 | Nestlerode et al. | |
| 4,948,770 A | * 8/1990 | Job ............... | 502/107 |
| 5,106,807 A | * 4/1992 | Morini et al. ............... | 502/121 |
| 5,221,651 A | * 6/1993 | Sacchetti et al. ............... | 502/126 |
| 5,290,745 A | 3/1994 | Jorgensen et al. | |
| 5,476,911 A | * 12/1995 | Morini et al. ............... | 526/124.6 |
| 5,488,022 A | * 1/1996 | Takahashi et al. ............... | 502/115 |
| 5,652,314 A | 7/1997 | Wagner et al. | |
| 5,780,378 A | * 7/1998 | Toida et al. ............... | 502/126 |
| 6,034,025 A | 3/2000 | Yang et al. | |
| 6,111,038 A | * 8/2000 | Kioka et al. ............... | 526/123.1 |
| 6,329,454 B1 | 12/2001 | Krabbenborg | |
| 2004/0010101 A1 | * 1/2004 | Wagner et al. ............... | 526/124.3 |

FOREIGN PATENT DOCUMENTS

KR    WO 02/053604 A1 *  7/2002   ............... C08F/4/64

* cited by examiner

Primary Examiner—Mark L. Bell
Assistant Examiner—Jennine M. Brown
(74) Attorney, Agent, or Firm—Osborne K. McKinney

(57) ABSTRACT

A magnesium halide composition comprising and/or made from a magnesium halide, a solvent suitable for an electron donor compound and an electron donor compound. The composition is characterized by enhanced solubility whereby it has a solubility in the solvent that does not decrease as a function of temperature up to the boiling point of the solvent and the solubility of the magnesium halide in the solvent is greater than 0.7 mol/liter. A polymerization catalyst precursor composition can be made from magnesium halide composition by mixing the magnesium halide composition with a transition metal compound.

14 Claims, 4 Drawing Sheets

Solubility Profiles for EtOH-modified MgCl2 in THF

ENHANCED SOLUBILITY OF MAGNESIUM HALIDES AND CATALYSTS AND POLYMERIZATION PROCESS USING SAME

CROSS REFERENCE TO RELATED APPLICATIONS

Not Applicable.

FEDERALLY SPONSORED RESEARCH

Not Applicable.

REFERENCE TO MICROFICHE APPENDIX

Not Applicable.

FIELD OF THE INVENTION

This invention relates to magnesium halide compositions, catalysts made therefrom, methods of increasing the solubility of magnesium halides, methods of making magnesium halide compositions and catalysts, as well as methods of polymerization.

BACKGROUND OF THE INVENTION

Solutions of $MgCl_2$ in various electron donor solvents have found use in industry for the preparation of olefin polymerization catalysts. Often these solutions employ ethers, ketones and esters to form Mg—Ti catalyst precursors that have found wide acceptance in the catalysis of olefin polymerizations. Known precursors have resulted from the dissolution of magnesium chloride and titanium chloride in the solvent, followed by evaporation or distillation of the excess solvent. Tetrahydrofuran (TMF) has proven an especially useful solvent due to its coordinating properties with both $MgCl_2$ and $TiCl_x$ and its relatively low boiling point, which facilitates evaporation and solvent recovery. The resulting dried catalyst precursor is treated with a cocatalyst, typically an aluminum alkyl compound, to generate the composition which is active in olefin polymerization.

The use of such catalyst precursors in industrial polymerization processes exploit the solubility of $MgCl_2$ in the solvent. Alkaline-earth halides are typically insoluble in hydrocarbon solvents However the solubility in certain coordinating electron donor solvents can be suitably high for industrial applications For instance, the solubility of $MgCl_2$ in tetrahydrofuran (THF) increases from ca 0.2 M at $-25°$ C. to about 0.7 M at $30°$ C. The amount of precursor that is obtainable per batch preparation of precursor is limited by the solubility of $MgCl_2$.

Interestingly, however, at higher temperatures, the solubility of $MgCl_2$ in such donor solvents decreases. For example, at the boiling point of THF ($65°$ C.) the solubility of $MgCl_2$ is only about 0.4 M at atmospheric pressure. Such a reduction in solubility complicates the precursor drying process because removal of the solvent by heating is typically performed most effectively near the boiling point of the solvent. To avoid reducing the concentration of $MgCl_2$ in the precursor solution to undesirable levels, the drying process is performed at reduced temperatures and pressures. Unfortunately, removal of the solvent under these conditions requires more time and is less effective, thereby reducing batch throughput.

The reduced solubility of $MgCl_2$ at higher temperatures also causes the formation of a thick crust of precipitated $MgCl_2$ on reactor walls and piping when solubility limits are exceeded at such temperatures.

For these reasons, catalyst precursor systems with improved solubility would find use in polymerization processes. Also, methods of increasing the solubility and changing the solubility profile of $MgCl_2$ as a function of temperature would be useful. Therefore, magnesium halide catalyst components having higher solubility or a solubility that does not decrease with temperature and processes employing such catalyst components and catalysts made therefrom would be useful.

SUMMARY OF THE INVENTION

In some embodiments, there is provided a method for increasing the solubility of a magnesium halide, comprising 1) providing an electron donor solvent; contacting a magnesium halide with the electron donor solvent, and 2) providing an electron donor compound to form a magnesium-halide composition, wherein the composition is characterized by a solubility of the magnesium halide in the solvent that does not decrease as a function of the temperature up to the boiling point of the solvent In other embodiments, a polymerization catalyst component comprising a magnesium halide, an electron donor solvent, and an electron donor compound, wherein the composition is characterized by a solubility in the electron donor solvent that does not decrease as a function of the temperature up to the boiling point of the electron donor solvent is provided.

In still other embodiments, a method of making a catalyst is disclosed In such embodiments, the method comprises forming a magnesium-containing composition, contacting the magnesium-containing composition with a transition metal compound to form a catalyst precursor, and contacting the catalyst precursor with a cocatalyst. The magnesium-containing composition includes a magnesium halide, an electron donor solvent, and an electron donor compound and is characterized by a solubility in the electron donor solvent that does not decrease as a function of the temperature up to the boiling point of the electron donor solvent.

Still other embodiments provide methods of making a polymer, comprising reacting at least one olefin monomer in the presence of a catalyst comprising the reaction product of: a magnesium-containing composition that includes a magnesium halide, an electron donor solvent, and an electron donor compound. The magnesium-containing composition is characterized by a solubility in the electron donor solvent that does not decrease as a function of the temperature up to the boiling point of the electron donor solvent. The catalyst composition also includes a transition metal compound, wherein the transition metal is selected from the group consisting of titanium, zirconium, hafnium, vanadium, niobium, tantalum, and combinations thereof, and a cocatalyst composition.

In some embodiments described above, compositions are substantially free of other electron donor compounds, and the molar ratio of the electron donor compound to magnesium halide is less than or equal to 1.9. In some embodiments, the ratio of the electron donor compound to magnesium halide is less than about 1.75, while in others the ratio of the electron donor compound to magnesium halide ranges from about 0.1 to less than about 0.5.

In some methods, catalyst precursors, catalyst components, and catalysts described herein, the magnesium halide is magnesium chloride, magnesium bromide, magnesium iodide, or combinations thereof. The electron donor compound may be a linear, branched, substituted, or unsubstituted aliphatic or aromatic alcohol having between one and about 25 carbon atoms. Exemplary alcohols include methanol, ethanol, propanol, isopropanol, butanol, 2-ethyl hexanol, 1-dodecanol, cyclohexanol, and di-tert-butyl phenol.

The solvent may be selected from the group consisting of alkyl esters of aliphatic and aromatic carboxylic acids, aliphatic ethers, cyclic ethers, and aliphatic ketones. In some embodiments, the solvent is selected from the group consisting of alkyl esters of aliphatic and aromatic carboxylic acids, ethers, and aliphatic ketones. Exemplary alkyl esters suitable as solvents include methyl acetate, ethyl acetate, ethyl propionate, methyl propionate, ethyl benzoate, and combinations thereof. Ethers that are suitable for use as the solvent include, but are not limited to, diethyl ether, diusopropyl ether, di-n-butyl ether, ethylisopropyl ether, methylbutyl ether, methylallyl ether, ethylvinyl ether, tetrahydrofuran, 2-methyl tetrahydrofuran and combinations thereof Suitable ketones include acetone, methylethyl ketone, cyclohexanone, cyclopentylmethyl ketone, 3-bromo-4-heptanone, 2-chlorocyclo-pentanone, allylmethyl ketone, and combinations thereof Of course, mixed solvents containing a second electron donor solvent that is an alkyl ester of an aliphatic or aromatic carboxylic acid, an aliphatic or cyclic ether, or an aliphatic ketone may be used in some embodiments. In some embodiments described herein, the solubility of a magnesium halide composition in solvent is greater than about 0.7 mol/liter.

In particular embodiments, the magnesium halide is magnesium chloride, the alcohol is ethanol or isopropanol, the molar ratio of the alcohol to magnesium is about 0.1 to about 1.1, the solubility of the magnesium halide or magnesium halide composition in the solvent is between about 0.8 and 2.5 mol $MgCl_2$/liter.

Some embodiments provide a catalyst component comprises a composition of the formula

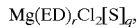

$Mg(ED)_r Cl_2 [S]_q$, wherein r is greater than 0 and less than 1.9, and q is greater than 0 and less than 4.

Some catalyst precursors described herein include compositions comprising reaction product of or mixture of the magnesium-containing catalyst component with a solubility in the solvent that does not decrease with temperature up to the boiling point of the solvent and a second component comprising a transition metal selected from the group consisting of titanium, zirconium, hafnium, vanadium, niobium, tantalum, and combinations thereof. Some exemplary such second components include at least one titanium compound having a formula of $Ti(OR^+)_a X_b$, wherein $R^+$ is $R^+$, or $COR^+$, where $R^+$, is individually a C1 to C14 aliphatic hydrocarbon radical or a C6 to C14 aromatic hydrocarbon radical; each X is individually Cl, Br, or I; a is 0 or 1; b is 2 to 4 inclusive; and a+b=3 or 4. In some embodiments, the at least one titanium compound comprises a titanium halide, such as, but not limited to, $TiCl_4$, $TiCl_3$, or aluminum reduced $TiCl_3$.

In certain embodiments, catalyst precursor compositions comprise a composition of the formula $[Mg(ED)_r]_m Ti(OR)_n X_p [S]_q$, wherein ED comprises a linear or branched alcohol having between one and about 25 carbon atoms; X is individually Cl, Br, or I; S is selected from the group consisting of alkyl esters of aliphatic and aromatic carboxylic acids, aliphatic ethers, cyclic ether, and aliphatic ketones, m ranges from 0.5 to 56; n is 0, 1, or 2; p ranges from 4 to 116; q ranges from 2 to 85, and r ranges from 0.1 to 1.9.

Some embodiments provide a catalyst that is the reaction product of a catalyst precursor and a cocatalyst. Other embodiments further include modifying the catalyst with a Lewis acid. Some suitable Lewis acids have the formula

$R_g^* MX_{3-g}$, wherein $R^*$ is a $R^{*1}$ or $OR^{*1}$; wherein $R^{*1}$ is an aliphatic hydrocarbon having from 1 to 14 carbon atoms or an aromatic hydrocarbon radical containing from 6 to 14 carbon atoms; M is Al or B; X is Cl, Br, or I; and g ranges from 0 to 3. Exemplary chloride-based Lewis acids include tri-n-hexyl aluminum, triethyl aluminum, diethyl aluminum chloride, ethyl aluminum dichloride, trimethyl aluminum, dimethyl aluminum chloride, methyl aluminum, dichloride, triisobutyl aluminum, tri-n-butyl aluminum, diisobutyl aluminum chloride, isobutyl aluminum dichloride, ethoxy aluminum dichloride, phenyl aluminum dichloride, and phenoxy aluminum dichloride. Exemplary bromine-containing Lewis acids include diethyl aluminum bromide, ethyl aluminum dibromide, dimethyl aluminum bromide, methyl aluminum, dibromide, diisobutyl aluminum bromide, isobutyl aluminum dibromide, ethoxy aluminum dibromide, phenyl aluminum dibromide, and phenoxy aluminum dibromide Iodide-based Lewis acids include diethyl aluminum iodide, ethyl aluminum diiodide, trimethyl aluminum iodide, methyl aluminum, diiodide, diisobutyl aluminum iodide, isobutyl aluminum diiodide, ethoxy aluminum diiodide, phenyl aluminum diiodide, and phenoxy aluminum diiodide.

Other suitable Lewis acids include boron trichloride, boron tribromide, ethyl boron dichloride, ethoxy boron dichloride, diethoxy boron chloride, phenyl boron dichloride, phenoxy boron dichloride, diphenoxy boron chloride, $(C_6H_{13})BCl_2$, or $(C_6H_{13}O)BCl_2$ Still other suitable Lewis acids or cocatalysts follow the formula

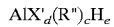

$AlX'_d(R'')_c H_e$ wherein X' is Cl or OR'''; R'' and R''' are individually C1 to C14 saturated hydrocarbon radicals, d is 0 to 1.5; e is 0 or 1; and c+d+e=3. Exemplary such activators include $Al(CH_3)_3$, $Al(C_2H_5)_3$, $Al(C_2H_5)_2Cl$, $Al(i-C_4H_9)_3$, $Al(C_2H_5)_{1.5}Cl_{1.5}$, $Al(i-C_4H_9)_2H$, $Al(C_6H_{13})_3$, $Al(C_8H_{17})_3$, $Al(C_2H_5)_2H$, $Al(C_2H_5)_2(OC_2H_5)$. In some embodiments one or more activators are present at an activator to transition metal compound ratio ranging from about 1 to about 400 moles of activator per mole transition metal compound. In some embodiments, the activator to transition metal compound ratio is about 4, about 10, about 15 or about 60 moles of activator per mole transition metal compound.

Some polymerization methods described herein provide polymers with a density ranging from about 0.88 to about 0.98 g/cm³. Some polymers have greater than or equal to about 90 mol percent ethylene and less than or equal to about 10 mol percent of one or more comonomers.

DESCRIPTION OF EMBODIMENTS OF THE INVENTION

Figure 1:
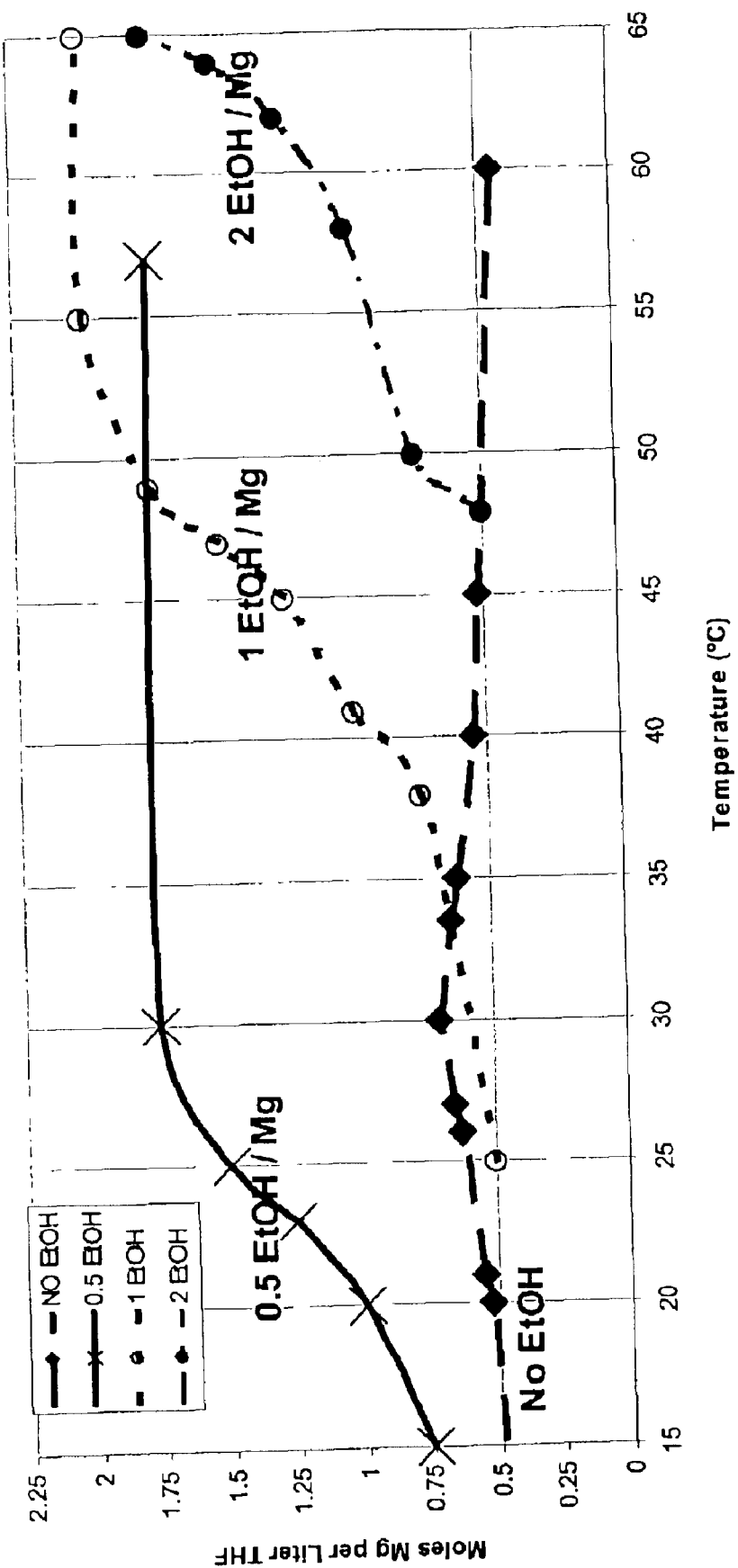
FIG. 1 illustrates solubility behavior of $MgCl_2$ solutions for three embodiments of the invention in THF as a function of alcohol content and solution temperature.

Embodiments of the invention provide a method for increasing the solubility of a magnesium halide that includes providing an electron donor solvent, contacting a magnesium halide with the solvent, and providing an electron donor compound to form a magnesium halide composition wherein the composition is characterized by a solubility in the solvent that does not decrease as a function of the temperature up to the boiling point of the solvent. Catalyst components having a solubility that does not decrease with increasing temperature are provided. Embodiments of the invention that provide catalyst precursors incorporating such catalyst components are disclosed. Methods of making such compounds, as well as polymerization catalysts and polymerization methods employing such catalysts are also disclosed.

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit, $R_U$, is disclosed, any number R falling within the range is specifically disclosed. In particular, the following numbers R within the range are specifically disclosed: $R=R_L+k*(R_U-R_L)$, wherein k is a variable ranging from 1% to 100% with a 1% increment, i.e. k is 1%, 2%, 3%, 4%, 5%, ..., 50%, 51%, 52%, ..., 95%, 96%, 97%, 98%, 99%, or 100%. Moreover, any numerical range defined by two numbers, R, as defined above, is also specifically disclosed.

Any reference herein to "electron donor compounds" refers to compounds that modify the solubility of a magnesium halide in the electron donor solvent so that the solubility does not decrease over any temperature interval up to the boiling point of the electron donor solvent. As used herein, "electron donor compounds" do not include "solvents" as they are defined below, even when such solvents have electron donor character. Exemplary electron donor compounds include alcohols, thiols, weakly donating amines and phosphines. As used herein, the term "substantially free of other electron donor compounds" means that other "electron donor compounds," as defined herein, are not present at concentrations higher than levels normally found as impurities in solvent-grade supplies of such compounds. Thus, compositions having a solvent with electron donating characteristics and an "electron donor compound" are considered to be "substantially free of other electron donor compounds." In some embodiments, "substantially free of" means less than 1%, 0.1%, 0.01%, or 0.001%.

Useful solvents include any ether, ketone, or ester compound While such solvents possess electron donor characteristics, any reference herein to a "solvent" or "solvents" does not include those compounds defined above as "electron donor compounds." Thus, compositions that are "substantially free of other electron donor compounds" may include one or more "solvents."

As used herein, the term "ether" is defined as any compound of the formula R—O—R', where R and R' are substituted or unsubstituted hydrocarbyl groups. In some cases, R and R' are the same. Exemplary, but not limiting, symmetric ethers are diethyl ether, diisopropyl ether, and di-n-butyl ether. Exemplary nonsymmetric ethers include ethylisopropyl ether and methylbutyl ether. Examples of suitable substituted ethers include, for example, methylallyl ether and ethylvinyl ether. In still other embodiments, R and R' may form a fused ring that may be saturated or unsaturated. One example of such a compound is tetrahydrofuran. Another such suitable cyclic ether is 2-methyl tetrahydrofuran. Again, specifically enumerated compounds are intended only as examples of types of compounds that are suitable; however, any compound having ether R—O—R' functionality is envisioned.

As used herein, the term "ketone" is intended to indicate any compound having the formula R(C=O)R'. R and R' may be individually substituted or unsubstituted hydrocarbyl groups, as described above with reference to ethers. Exemplary ketones are acetone, methylethyl ketone, cyclohexanone, and cyclopentylmethyl ketone. Halogenated ketones, such as 3-bromo-4-heptanone or 2-chlorocyclopentanone may also be suitable. Other suitable ketones may include other functional groups such as unsaturations, as in allylmethyl ketone. Each of these compounds fits the formula R(C=O)R', wherein the carbon atom of the carbonyl group of the molecule forms bonds to two other carbon atoms.

Useful esters include any compound of the general formula R(C=O)OR'. In such compounds, the carbon atom of the carbonyl group forms one bond to a carbon atom and another bond to an oxygen atom. R and R' are individually selected from substituted or unsubstituted hydrocarbyl groups and may be the same or different. In some embodiments, the esters include alkyl esters of aliphatic and aromatic carboxylic acids. Cyclic esters, saturated esters, and halogenated esters are also included in this group. Exemplary, but non-limiting, esters include methyl acetate, ethyl acetate, ethyl propionate, methyl propionate, and ethyl benzoate. Again, specifically enumerated compounds are intended only as examples of types of compounds that are suitable. Any compound meeting the general formula R(C=O)OR' functionality is envisioned Generally, the solvent is provided in large excess with respect to the first coordination environment of magnesium. In some embodiments, the ratio of solvent to magnesium is about 100 to 1; in other embodiments, the ratio may be even larger. In yet other embodiments, the solvent is present at a ratio of from at least about 1.0, at least about 2.0, at least about 5.0, at least about 10, or at least about 20 moles of solvent per mole of magnesium. In some embodiments, two or more solvents may be employed.

Contacting a magnesium halide with any suitable solvent is accomplished by directly mixing the magnesium halide and the solvent. In some embodiments, the magnesium halide is magnesium chloride; however, magnesium bromine and magnesium iodine may also be used. Useful sources of the halides are magnesium halides, such as $MgCl_2$, $MgBr_2$, $MgI_2$, or mixed magnesium halides such as MgClI, MgClBr, and MgBrI. In some embodiments, the magnesium halide is added to the solvent in anhydrous form. In other embodiments, the magnesium halide is added in a hydrated form.

An electron donor compound is added to the mixture of the solvent and the magnesium halide by any suitable means. Preferably, the electron donor compound is directly added to the mixture. In some embodiments, the electron donor compound is an alcohol, thiol, weakly donating amine, or weakly donating phosphine. The alcohol can be any one chemical compound having a general formula ROH. R may be any substituted or unsubstituted hydrocarbyl group. In some embodiments, the alcohol is an aliphatic alcohol with from about 1 to about 25 carbon atoms. In some embodiments, the alcohol is a monodentate alcohol. As used herein, the term "monodentate alcohol" refers to those in which R may be provided that the substitution does not result in a molecule with more than one hydroxyl (OH) functionality that coordinates to the magnesium atom in solution. Exemplary such alcohols may include methanol, ethanol, propanol, isopropanol, and butanol. Alcohols containing a longer chain aliphatic group, such as 2-ethyl hexanol or 1-dodecanol, also form solutions in which the solubility of the magnesium halide increases with temperature. Alcohols with more carbon atoms are also useful. The alcohol may also be a cyclic alcohol, such as cyclohexanol, or an aromatic alcohol, such as phenol.

In certain embodiments, the ratio of the electron donor compound to the magnesium halide is less than or equal to 1.9 In some embodiments, the molar ratio of the alcohol to magnesium is less than about 1.75, less than 1.5, less than 1.0, less than 0.75, less than 0.5, less than about 0.4, or less than about 0.25 In still other embodiments, the molar ratio of the electron donor to the magnesium is about 0.1. In other embodiments, the molar ratio may be higher than 1.9, such as about 2.0, about 2.1, about 2.2, about 2.5, and about 3.0.

The addition of small amounts of one electron donor compound, other than the solvent, to mixtures containing the solvent and a magnesium halide produces a magnesium-containing composition whose solubility increases with temperature and whose solubility at the boiling point of solvents is relatively higher than that of magnesium halide/electron donor adducts where no electron donor compound is present. The solubility is also higher than that of comparable magnesium halide/electron donor adducts having additional kinds of electron donor compound. It is believed that the addition of small amounts of one electron donor to the solvent in the presence of a magnesium halide suppresses the conversion of soluble species to polymeric adducts. In some embodiments, the soluble species follow the formula

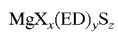

wherein x is generally 2, satisfying the oxidation state of magnesium and y is less than 4, and x+y+z is less than or equal to 6. In some embodiments, y is about 0.5, 0.75, 1, 1.5, 1.75, 1.9, or less In some other embodiments, y is about 0.1, 0.25, 0.3, or 0.4. Such species generally have solubilities in the solvent that increase with temperature up to the boiling point of the solvent. Where the solvent is THF, the concentration of magnesium halide in the solution may be up to five times higher than in comparable solutions lacking an electron donor compound, especially where the electron donor compound is an alcohol.

FIG. 1 illustrates the solubility profile of magnesium chloride solutions as a function of temperature in tetrahydrofuran and an alcohol. As FIG. 1 illustrates, compositions having no alcohol generally have a solubility of magnesium halide that increases from about 0.5 moles magnesium per liter to a maximum of less than about 0.65 moles magnesium per liter at about 30° C. Above 30° C. the solubility gradually decreases until the boiling point of the solvent is reached. In contrast, mixtures to which an alcohol, such as ethanol, has been added have a solubility of magnesium halide that does not decrease as the temperature is increased up to the boiling point of the solvent. For instance, mixtures having a ratio of ethanol to magnesium of about 0.5 show that the solubility of magnesium at 15° C. is about 0.75 mol/liter. The solubility of magnesium chloride increases as the temperature increases up to about 30° C., where the concentration of magnesium in solution is about 1.75 moles/liter. As the temperature is increased above 30° C., the solubility remains substantially constant until the boiling point is reached.

FIG. 1 also illustrates the solubility behavior of mixtures having a ratio of alcohol to magnesium of about 1. At 25° C. the concentration of magnesium present in solution is about 0.5 moles/liter. However, the concentration increases to about 2 moles/liter by the time the temperature reaches about 55° C. and remains substantially constant up to the solvent boiling point. Samples having a ratio of two moles of alcohol to magnesium also show that the solubility of the magnesium increases as a function of temperature up to the boiling point where the value is about 1.75 moles of magnesium per liter.

Figure 2:
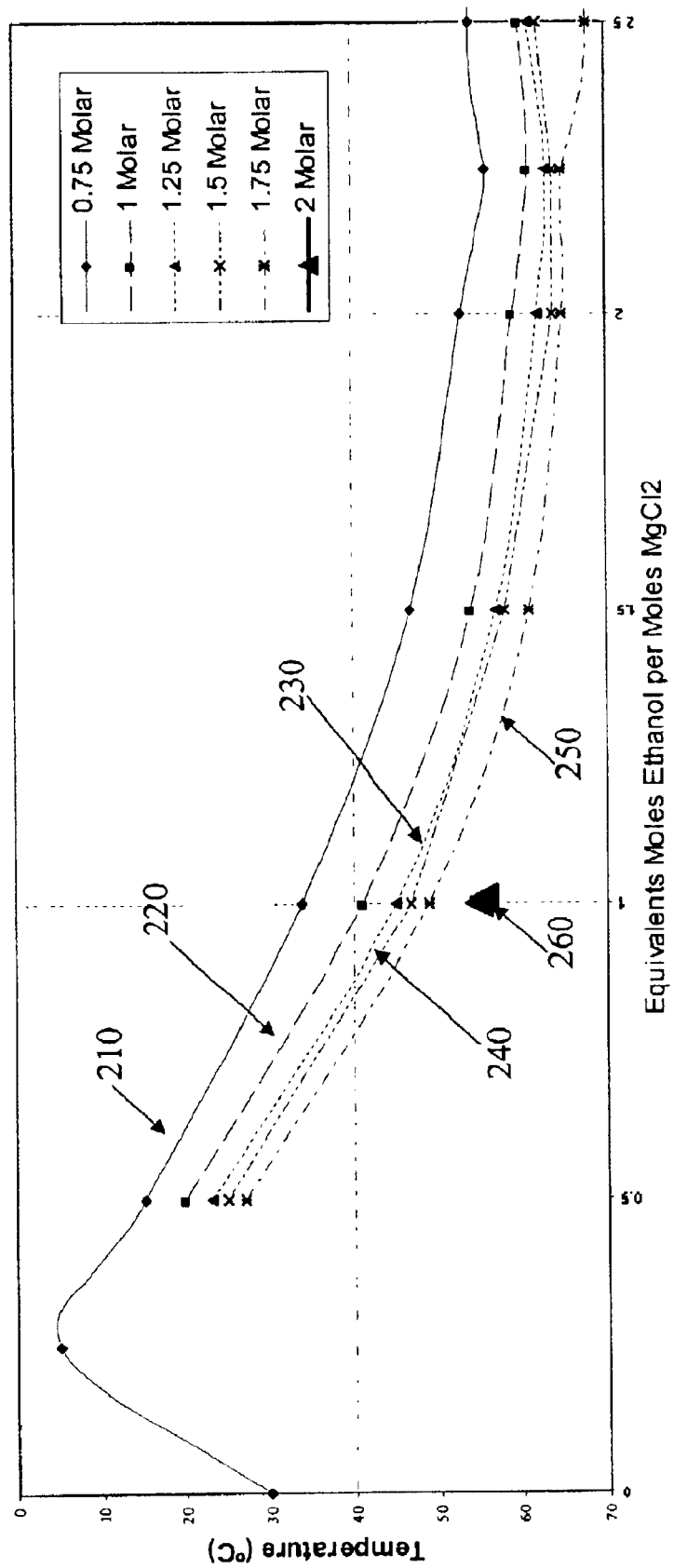
FIG. 2 illustrates the solubility profile of several embodiments of the invention as a function of temperature, $MgCl_2$ concentration, and alcohol Mg ratio THF.

FIG. 2 illustrates the solubility profile of several mixtures containing different amounts of added alcohol. Each point of data in FIG. 2 was generated by adding the amount of magnesium chloride needed to achieve the desired concentration when all the magnesium chloride dissolved in THF. A portion of alcohol was then added to give the desired alcohol:magnesium ratio, and the mixture was heated until the composition dissolved. The solution was then slowly cooled until a precipitate began to form The temperature at which the precipitate begins to form is recorded as the y axis in FIG. 2. Thus, FIG. 2 shows the temperature needed to prepare magnesium chloride solutions of different concentrations in the presence of an alcohol. For instance, data set 210 illustrates the temperature necessary to achieve a solution that is about 0.75M in magnesium chloride where the solvent is THF in the presence of different concentrations of ethanol. In mixtures prepared with an alcohol to magnesium ratio of 0.25, the concentration of magnesium in solution is about 0.75M at only 5° C. Mixtures prepared with a ratio of alcohol to magnesium chloride ratio of 0.5 reach a concentration of 0.75M in magnesium at about 15° C., while a mixture with a ratio of 1.0 reaches 0.75M at about 33° C. Where the mixture is prepared to have a ratio of 1.5 or 2.0 moles of alcohol to magnesium chloride, the solutions achieve a magnesium concentration of about 0.75M at about 47° C. and 53° C., respectively. Thus, data set 210 indicates that mixtures with higher alcohol magnesium ratios tend to be less soluble.

Thus, FIG. 2 illustrates that smaller ratios of alcohol to magnesium chloride produce solutions with a higher concentration of dissolved magnesium. The decrease in solubility with increasing ROH/MgCl$_2$ ratio suggests that small amounts of added ROH prevent the formation of the polymeric MgCl$_2$(THF)$_2$ adduct, and addition of larger amounts of ROH, or additional alcohols, drives the solution towards less soluble adducts containing more ROH. The ratio of ROH/Mg employed determines the maximum solubility that can be reached and the temperature needed. Data sets 220–260 of FIG. 2 indicate that for a given alcohol:magnesium ratio, increasing the temperature increases the amount of magnesium that is soluble. For example, solutions with an alcohol:magnesium molar ratio of 0.5 have a concentration of magnesium in solution of about 0.75 M at about 15° C., while at about 20° C. a 1.0 M concentration of magnesium in solution is obtainable. Line 230 shows that at about 23° C. the same solution can dissolve about 1.25 moles/liter of magnesium chloride. FIG. 2 also shows that the solubility of magnesium chloride in such solutions also increases for temperatures above 30° C. For instance, solutions having a molar ratio of alcohol to magnesium of 1 show that at a temperature of about 35° C. the solubility of magnesium chloride is about 0.75M while at about 41° C. the solubility increases to about 1M. The data of lines 230–260 show indicate that the solubility continues to increase as the boiling point of the THF is approached. Solutions having higher ratios of alcohol:magnesium display similar behavior The nature of the species in solution has been elucidated by a variety of characterization methods. NMR studies indicate that electron donors coordinated to $MgCl_2$ in THF solution are in rapid equilibrium, and no individual long-lived species exists. The gas phase over a THY solution containing $MgCl_2$ and 2 equivalents of ethanol (EtOH) per Mg contains significantly less alcohol than the gas phase over the same EtOH/THF solution not containing $MgCl_2$. This suggests that the ethanol is sequestered by the $MgCl_2$ molecules in the solution. It is apparent that the alcohol functionality is coordinated to the $MgCl_2$ center in the solution phase. The maximum solubility at intermediate alcohol. $MgCl_2$ ratios suggests that several species are in solution whose concentration depends on the identity of the alcohol, the specific alcohol:Mg ratio, and on the temperature of the solution.

Figure 3:
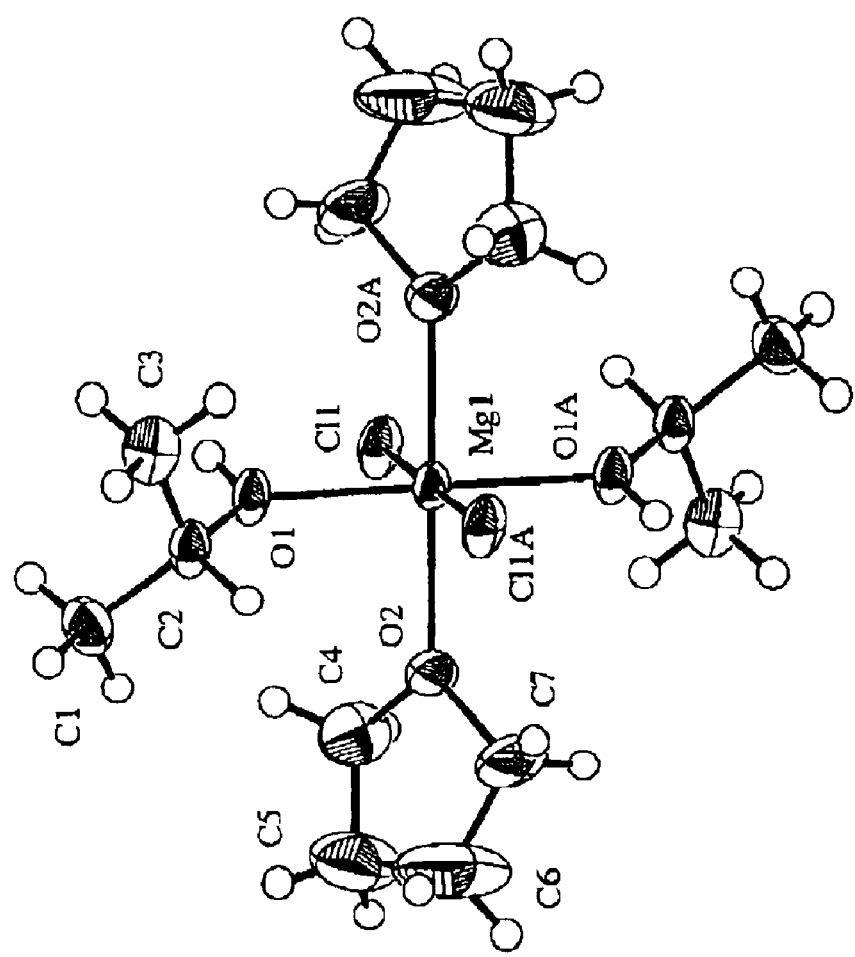
FIG. 3 illustrates the structure of an exemplary magnesium halide-containing catalyst component.

FIG. 3 illustrates the x-ray, single crystal structure of an exemplary catalyst component isolated as a solid. As FIG. 3 illustrates, this component comprises a magnesium-centered molecule. In this embodiment, the precursor has two THF solvent molecules bonded to the magnesium, as well as two halides in the form of chlorine and two alcohol ligands. Thus, the component has the formula $MgCl_2ROH_2THF_2$, in which ROH is isopropyl alcohol. Analogous compounds where ROH is ethanol can also be isolated. In this particular embodiment, the structure illustrated is generally referred to as a trans-octahedral magnesium-centered structure since ligands of the same type are related through a center of symmetry on the magnesium atom. However, such a structure is not required for any embodiment of the catalyst component. In other embodiments, the precursor may be mixtures of two or more individual compounds. For example, in one embodiment, the component may comprise mixtures of $MgCl_2ROH/THF_3$ and $MgCl_2ROH_2THF_2$. Any number of individual compounds is envisioned so long as the mixture as a whole satisfies the formula $MgX_x(ED)_yS_z$ where y is less than or equal to 1.9.

In other embodiments, the magnesium halide catalyst component has a formula according to

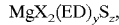

$MgX_2(ED)_yS_z$, where y+z is less than or equal to 4 and y is less than or equal to 1.9. In those embodiments where y+z is less than 4, the catalyst component may be considered solvent deficient. These compositions may also be referred to as non-stoichiometric compositions. These compositions may be obtained in solid form from the fully coordinated $MgCl_2(ROH)_2(THF)_2$ or other $MgX_x(ED)_yS_z$ composition by heating, applying reduced pressure, or combinations of both.

Figure 4:
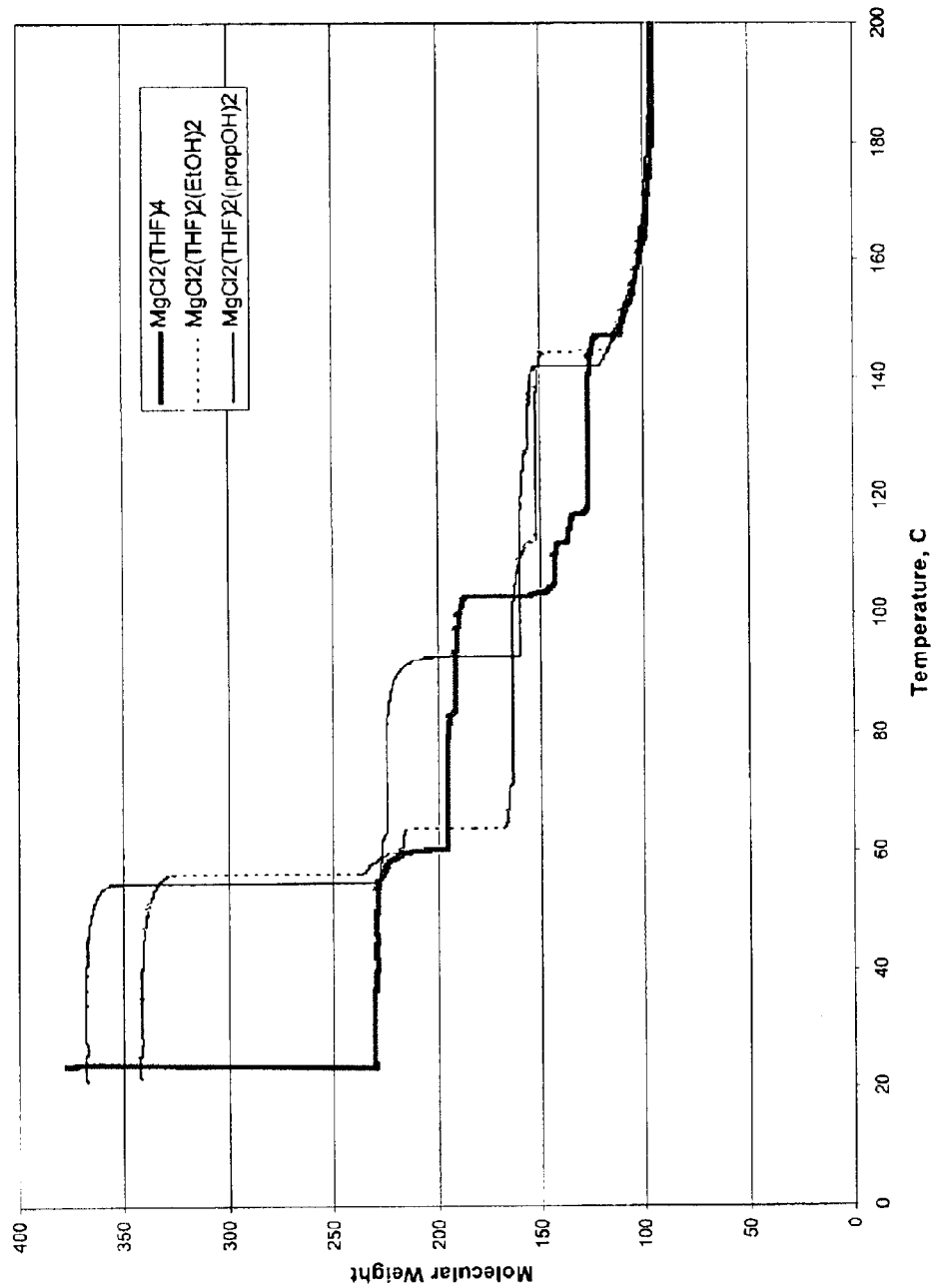
FIG. 4 illustrates the thermogravimetric analysis (TGA) behavior for embodiments of the inventive catalyst component.

FIG. 4 illustrates thermogravimetric analysis (TGA) measurements showing the behavior of $MgCl_2(ROH)_2(THF)_2$. TGA measurements were made at a heating rate of 10° C./minute during periods when no weight loss is measured. In periods where the sample is losing mass, the temperature ramp was eliminated until no further weight loss was measured. As FIG. 4 indicates, most of the solvent and alcohol can be stripped off by heating the composition to 50° C.–200° C., with one of the THF molecules being lost first, followed by both ROH and THF. A variety of porous $MgCl_2$-containing compositions suitable for forming porous catalyst components can be formed in this way. Thus, in some embodiments, the catalyst component may have a coordinatively unsaturated and polymeric, rather than a monomeric, structure.

In another aspect, a method for preparing the catalyst components described above is disclosed. Methods for preparing the catalyst components include providing a solvent, contacting a magnesium halide with the solvent, and adding an electron donor compound to form the polymerization catalyst component. In some embodiments, the molar ratio of the electron donor compound to magnesium is less than or equal to 1.9. In other embodiments, especially where the electron donor compound is alcohol, the ratio of alcohol to magnesium may be greater than 1.9, such as about 2.0, about 2.1, about 2.2, about 2.5, or about 3.0. In some embodiments, the method may also include isolating the polymerization catalyst component. Embodiments of the method may also include removing a portion of the solvent or alcohol from the isolated polymerization catalyst component. In certain embodiments, the removal of the solvent or alcohol may be accomplished by applying heat, vacuum, or a combination of both.

Contacting a magnesium halide with the solvent is typically accomplished by physical mixing or the magnesium halide solid with the electron donating compound or solution thereof. The contacting may include stirring, or other mechanical agitation. In some embodiments, mixing is facilitated by applying ultrasonic frequencies to the resulting mixture. The magnesium halide may be any of the magnesium halide compounds enumerated above and may be prepared as a solid or as a slurry.

Adding the electron donor compound is, in some embodiments, accomplished by the direct addition. In other embodiments, the electron donor is supplied as a solution. Alcohols that are suitable for as the electron donor compound include any of the alcohols having the formula ROH as defined above. The total quantity of the alcohol that is added to the solution is determined from the amount of magnesium. In some embodiments the molar ratio of alcohol to magnesium ranges from greater than zero to less than or equal to 1.9 In other embodiments, the ratio may be greater than 1.9. In still other embodiments, the ratio ranges from about 0.1 to about 1.75 In other embodiments, the ratio is about 0.25, 0.3, 0.4, or about 0.5 to 1.

Forming a polymerization catalyst precursor once the components are combined may be performed in any manner. In some embodiments, the components are combined at a temperature ranging from about −10° C. to about 200° C. In other embodiments, they may be contacted at 0° C. to about 160° C. Preferably, the temperature should be below the boiling point of the solvent. In some embodiments, the solvent, magnesium halide, and the alcohol may be allowed to react for from about 5 minutes to about 3 days. In other embodiments, 30 minutes to 5 hours are sufficient to achieve the desired concentration of magnesium in solution.

In some embodiments, low concentrations of alcohol allow the formation of solutions with previously unavailable concentrations of magnesium halides present in solution. The increased concentration of dissolved magnesium halide allows the preparation of more desirable polymerization catalysts because more magnesium halide may be incorporated into the catalyst.

Useful catalyst precursors are formed by reacting the catalyst component with a transition metal compound. Suitable transition metal compounds include compounds of Group III–VI transition metals. In some embodiments, the transition metal is titanium, zirconium or hafnium. In other embodiments, the metal is vanadium, niobium, or tantalum.

In certain embodiments, other transition metals, such as later transition metals and Lanthanides, may be suitable The transition metal compound may be supplied in a variety of compositions. Some embodiments employ titanium compounds having the general formula wherein titanium is in the +4 formal oxidation state. Titanium (IV) compounds useful in preparation of the catalyst components are titanium halides and haloalcoholates following the formula $Ti(OR)_aX_{4-a}$ wherein R is individually a substituted or unsubstituted hydrocarbyl group having 1 to about 25 carbon atoms group, such as methoxy, ethoxy, butoxy, hexoxy, phenoxy, decoxy, napthoxy, or dodecoxy; X is any halide; and a may range from 0 to 4. Mixtures of titanium compounds can be employed if desired.

In certain embodiments, the transition metal compound is selected from titanium compounds, halides, and haloacoholates having 1 to about 8 carbon atoms per alcoholate group. Examples of such compounds include $TiCl_4$, $TiBr_4$, $TiI_4$, $Ti(OCH_3)Cl_3$, $Ti(OC_2H_5)Cl_3$, $Ti(OC_4H_9)Cl_3$, $Ti(OC_6H_5)Cl_3$, $Ti(OC_6H_{13})Br_3$, $Ti-(OC_8H_{17})Cl_3$, $Ti(OCH_3)_2)Br_2$, $Ti(OC_2H_5)_2Cl_2$, $Ti(OC_6H_{13})_2Cl_2$, $Ti(OC_8H_{17})_2Br_2$, $Ti(OCH_3)_3Br$, $Ti(OC_2H_5)_3Cl$, $Ti(OC_4H_9)_3Cl$, $Ti(OC_6H_{13})_3Br$, and $Ti(OC_8H_{17})_3Cl$.

In other embodiments, the titanium compound is a reduced titanium halide. Useful reduced titanium halides follow the formula $TiCl_x$, wherein x ranges from greater than 0 to less than 4. In some embodiments, the reduced titanium compound is $TiCl_3$, $TiBr_3$, or $TiI_3$.

The quantity of a transition metal compound or mixture of transition metal compound, used in preparing catalyst precursors may vary widely depending on the type of catalyst desired. In some embodiments, the molar ratio of magnesium to transition metal compound may be as high as about 56, preferably about 20 to about 30. In other embodiments, the molar ratio of magnesium to transition metal compound is as low as about 0.5. Generally, molar ratios of magnesium to transition metal compound of about 3 to about 6 where the transition metal is titanium are preferred.

In some embodiments, a catalyst precursor is formed by the physical mixing of the magnesium halide component and the transition metal component. One such technique is ball-milling. In some embodiments, a solution of the magnesium halide component is combined with the transition metal compound. In other embodiments, the two components are combined by physical mixing techniques, such as, but not limited to ball-milling. In some embodiments, the combination of the magnesium halide component and the transition metal component forms a reaction product that may contain a variety of species, including the magnesium halide component and the transition metal compound. The reaction of the magnesium halide component with the transition metal compound may be performed at any suitable temperature. In some embodiments, the temperature may range from about −70° C. to about 100° C. In other embodiments, the temperature may be about −50° C. to about 50° C. After initiating the reaction, the temperature may be raised and the reaction allowed to proceed at 25° C. to about 150° for a period of from 30 minutes to about 5 hours. Of course, temperatures that cause decomposition of either of the components should be avoided.

In certain embodiments, the catalyst precursors comprise a composition of the formula

$[Mg(ROH)_r]_mTi(OR)_nX_p[S]_q$.

wherein ROH comprises a monofunctional, linear, or branched alcohol having between one and about 25 carbon atoms; R is R' or COR', wherein each R' is individually an aliphatic hydrocarbon radical having between 1 and about 14 carbon atoms or an aromatic hydrocarbon radical having between 1 and about 14 carbon atoms; X is individually Cl, Br, or I, S is selected from the group consisting of alkyl esters of aliphatic and aromatic carboxylic acids, aliphatic ethers, cyclic ether, and aliphatic ketones; m ranges from 0.5 to 56, n is 0, 1, or 2; p ranges from 4 to 116; q ranges from 2 to 85; and r ranges from 0.1 to 19

In some embodiments, the catalyst precursor may be treated with a Lewis acid. Generally, useful Lewis acid compounds have the structures $R_gAlX_{3-g}$ and $R_gBX_{3-g}$ wherein R is R', OR', or $NR'_2$, wherein R' is an aliphatic hydrocarbyl group containing 1 to 14 carbon atoms, or an aromatic hydrocarbyl radical containing from 6 to 14 carbon atoms; X is selected from the group consisting of Cl, Br, I, and mixtures thereof; and g in each case is 0–3

Suitable Lewis acid compounds include, but are not limited to, tri-n-hexyl aluminum, triethyl aluminum, diethyl aluminum chloride, trimethyl aluminum, dimethyl aluminum chloride, methyl aluminum dichloride, triusobutyl aluminum, tri-n-butyl aluminum, diiosbutyl aluminum chloride, isobutyl aluminum dichloride, $(C_2H)AlCl_2$, $(C_2H_5O)AlCl_2$, $(C_6H_5)AlCl_2$, $(C_6H_5O)AlCl_2$, $(C_6H_{13}O)AlCl_2$, and the corresponding bromine and iodine compounds.

Suitable boron halide compounds include, but are not limited to, $BCl_3$, $BBr_3$, $B(C_2H_5)Cl_2$, $B(OC_2H_5)Cl_2$, $B(OC_2H_5)_2Cl$, $B(C_6H_5)Cl_2$, $B(OC_6H_5)Cl_2$, $B(C_6H_{13})Cl_2$, $B(OC_6H_{13})Cl_2$ and $B(OC_6H_5)_2Cl$. Bromine and iodine-containing congeners of the above-listed compounds may also be used. The Lewis acids can be used individually or in combinations thereof.

Further details concerning Lewis acids which are suitable for the present purpose can be found in U.S. Pat. Nos. 4,354,009 and 4,379,758, which are incorporated by reference herein in their entirety.

In some embodiments, the catalyst may be treated with a cocatalyst. One or more aluminum alkyl compounds may be used. In some embodiments, the catalyst is partially activated. In such embodiments, enough activator should be employed to provide the catalyst with an activator compound/Ti molar ratio of 10:1, 8:1, or 4:1. This partial activation reaction can be carried out in a hydrocarbon solvent slurry followed by drying of the resulting mixture, to remove the solvent, at temperatures between about 20° C. and 80° C. In some embodiments, the partial activation may be carried out between about 50° C. and 70° C. Alternatively, a mineral oil slurry of the catalyst can be treated with the activator compound, and the resultant slurry can be fed into the reactor. Another alternative partial activation procedure is described in U S. Pat. No. 6,187,866, incorporated by reference herein in its entirety, in which the partial activation procedure occurs in a continuous fashion. The resulting product is either a free-flowing solid particulate composition or an oil slurry which can be readily fed to the polymerization reactor where the activation is completed with an additional activator compound which can be the same or different compound.

Activation of the modified catalyst is usually conducted in the polymerization reactor, although, in some embodiments the activation may be performed outside the polymerization reactor. When activation is conducted in the polymerization reactor, the activator compound and the catalyst are fed to the reactor through separate feed lines. Other liquid or gaseous feeds to the reactor may also be used to disperse the additional activator compound in the reactor. Compounds such as ethylene, nitrogen, and comonomer streams may be used. This solution may contain about 2, 5, 15, 20, 25, or 30 weight percent of the activator compound.

In other embodiments, the catalyst is further activated by treatment with an activator and may be added in the presence or absence of solvent. The additional activator compound is added to the unactivated or partially activated catalyst in such amounts to give a total Al/Ti molar ratio of about 10 to about 400. In some embodiments, the ratio of Al:Ti in the activated catalyst ranges from about 15 to about 60, or about 30 to about 100, or about 70 to about 200.

The activator compounds can be used individually or in combinations thereof and include compounds such as $Al(CH_3)_3$, $Al(C_2H_5)_3$, $Al(C_2H_5)_2Cl$, $Al(i-C_4H_9)_3$, $Al_2(C_2H_5)_3Cl_3$, $Al(i-C_4H_9)_2H$, $Al(C_6H_{13})_3$, $Al(C_2H_{17})_3$, $Al(C_2H_5)_2H$ and $Al(C_2H_5)_2(OC_2H_5)$.

The magnesium halide components, catalysts precursors, or catalysts described herein have a characteristic size distribution. As used herein, the terms "$D_{10}$," "$D_{50}$," and "$D_{90}$" indicate the respective percentiles of log normal particle size distribution determined by means of a Malvern 2600® particle size analyzer using a heptane as slurrying agent. Thus, particles having a $D_{50}$ of 12 µm have a median particle size of 12 µm. A $D_{90}$ of 18 lm indicates that 90% of the particles have a particle size of less than 18 µm, and a $D_{10}$ of 8 µm indicates that 10% of the particles have a particle size of less than 8 µm. The width or narrowness of a particle size distribution can be given by its span. The span is defined as $(D_{90}-D_{10})/(D_{50})$.

In some embodiments, the particles have a median particle size ranging from about 30 µm to about 5 microns. In some embodiments, the median particle size may be about 7 µm, about 8 µm, about 9 µm, or about 10 µm. In other embodiments, the median particle size is about 11 µm, about 12 µm, or about 13 µm. In still other embodiments, the median particle size may be about 15 µm, about 18 µm, about 20 µm, or about 25 µm. In some embodiments, the median particle size may decrease during measurement in the particle analyzer. Some embodiments of the precursors disclosed herein have a span ranging from about 1.5 to about 4.0. In some embodiments, the span may be greater or less than these values. Some particles will have a span of about 1.6, about 1.8, or about 2.0. Other embodiments have a span of about 2.2, about 2.4, about 2.6, about 2.8, or about 3.0. In other embodiments, the particles have a span of about 3.1, about 3.2, about 3.3, about 3.4, about 3.5, or about 3.75.

Yet other embodiments provide a method of making a polymer with the catalysts described above. In such embodiments, at least one olefin monomer is polymerized in the presence of a catalyst that includes magnesium, a halide, a solvent, an alcohol; and titanium wherein the catalyst is substantially free of other alcohols and wherein the molar ratio of the alcohol to magnesium is less than or equal to 1.9. The amount of catalyst to be employed varies depending on choice of polymerization technique, reactor size, monomer to be polymerized, and other factors known to persons of skill in the art and can be determined on the basis of the examples appearing hereinafter Polymerization processes should be carried out at temperatures sufficiently high to ensure reasonable polymerization rates and avoid unduly long reactor residence times, but not so high as to result in the production of sticky polymers due to excessive temperatures. Generally, temperatures range from about 0° C. to about 120° C. or 20° C. to about 110° C. In some embodiments, polymerization reactions are carried out at temperatures ranging from about 50° C. to about 110° C.

Alpha-olefin polymerizations are carried out at monomer pressures of about atmospheric or above. Generally, monomer pressures range from about 20 to about 600 psi.

The catalyst residence time generally ranges from about a few minutes to several hours in batch processes. Polymerization times ranging from about 1 to about 4 hours are typical in autoclave-type reactions. In slurry processes, the polymerization time can be regulated as desired. Polymerization times ranging from about a few minutes to several hours are generally sufficient in continuous slurry processes. Gas phase residence times are generally equal to slurry reactions Diluents suitable for use in slurry polymerization processes include alkanes and cycloalkanes, such as pentane, hexane, heptane, n-octane, isooctane, cyclohexane, and methylcyclohexane; alkylaromatics, such as toluene, xylene, ethylbenzene, isopropylbenzene, ethyl toluene, n-propylbenzene, diethylbenzenes, and mono- and dialkylnaphthalenes; halogenated and hydrogenated aromatics such as chlorobenzene, chloronaphthalene, ortho-dichlorobenzene, tetrahydronaphthalene, and decahydronaphthalene; high molecular weight liquid paraffins or mixtures thereof; and other well-known diluents. It often is desirable to purify the polymerization medium prior to use, such as by distillation, percolation through molecular sieves; contacting with a compound such as an alkylaluminum compound capable of removing trace impurities; or by other suitable means. Examples of gas-phase polymerization processes in which the catalyst in accordance with embodiments of the invention can be used are described in U.S. Pat. Nos. 3,957,448; 3,965,083; 3,971,768; 3,972,611; 4,129,701; 4,101,289; 3,652,527, and 4,003,712, which are incorporated herein by reference.

Polymerizations are carried out under conditions that exclude oxygen, water, and other compounds that act as catalyst poisons. In some embodiments, polymerization can be carried out in the presence of additives to control polymer molecular weights. Hydrogen is typically employed for this purpose in any suitable manner.

Upon completion of polymerization, or when it is desired to terminate polymerization or deactivate the catalysts, the catalyst can be contacted with water, alcohols, acetone, or other suitable catalyst deactivators in any suitable manner.

The molecular weight of the polymers is conveniently indicated using melt flow measurements. One such measurement is the melt index (MI), obtained according to ASTM D-1238, Condition E, measured at 190° C. with an applied load of 2.16 kilograms (kg), reported as grams per 10 minutes. Polymers prepared using some catalysts described herein have MI values ranging from about 0.01 to about 10,000 gram/10 min. Melt flow rate is another method for characterizing polymers and is measured according to ASTM D-1238, Condition F, using 10 times the weight used in the melt index test above. The melt flow rate is inversely proportional to the molecular weight of the polymer. Thus, the higher the molecular weight, the lower the melt flow rate, although the relationship is not linear. The melt flow ratio (MFR) is the ratio of melt flow rate to the melt index. This correlates with the molecular weight distribution of the product polymer. Lower MFRs indicates narrower molecular weight distributions. Polymers prepared using some catalysts described herein have MFR values ranging from about 20 to about 40.

Polymers may also be characterized by their density. Polymers herein may have a density of from about 0.85 to about 0.98 g/cm³, as measured in accordance with ASTM D-792 in which a plaque is made and conditioned for one hour at 100° C. to approach equilibrium crystallinity. Measurement for density is then made in a density gradient column.

In some embodiments, polymer yields are sufficiently high relative to the amount of catalyst employed so that useful products can be obtained without separation of catalyst residues. The polymeric products produced in the presence of the invented catalysts can be fabricated into useful articles by extrusion, injection molding, and other common techniques.

EXAMPLES

The following examples are given to illustrate various embodiments of the invention described herein. They should not be construed to limit the invention otherwise as described and claimed herein. All numerical values are approximate.

Solubility Studies.

To each of six 100-ml side-arm flasks equipped with a magnetic spin bar was added 5.09 g (25 mmol) of solid [$MgCl_2$* 1.5 THF] under $N_2$. The varying amounts of THF required to give the desired solution concentration of from 0.5M to 2.0M in magnesium was added to each flask, and the slurry was stirred for 5 minutes. Then was added 12.5 mmol (1.45 ml) of ethanol to give a 0.5 EtOH:Mg ratio. The mixtures were heated in a 60° C. oil bath and held at temperature for 2 hours to dissolve all $MgCl_2$, if feasible Samples were then allowed to cool to room temperature. Precipitated compounds were re-slurried and gradually reheated. The temperature at which the composition dissolved during the heating process was recorded. The solutions or slurries were allowed to cool to room temperature and the next increment of ethanol was added. The process was then repeated at this higher EtOH:Mg ratio. These experiments were likewise conducted with other alcohols.

$MgCl_2(EtOH)_1(THF)_x$ Study

In a 100 cc Schlenk flask with magnetic stir bar, 8.14 g of solid $MgCl_2(THF)_{1.5}$ (40 mmol Mg) were slurried under nitrogen in 20 cc THF at 22° C. over a water bath. A freely-stirring slurry was obtained To this slurry was added 2.3 cc (40 mmol) absolute ethanol to provide a 1:1 ROH:Mg ratio. The slurry thickened, but the suspended solids did not dissolve. On heating the slurry to 60° C., all of the solids dissolved to give a 2M solution of $MgCl_2$ with an alcohol:Mg ratio of 1:1 in solution. The solution was cooled slowly. At 45° C., the solution became cloudy, but no precipitate was observed. The flask and its contents were allowed to cool to ambient temperature without stirring, and crystals were allowed to grow for 2.5 days. A mass of white solids in a pool of solution was obtained. The slurry was filtered through a medium frit and rinsed quickly 3 times with 10 cc of ice cold THF, leaving fine needles and granular materials. The solids were dried overnight with $N_2$-purge at room temperature. Yield: 1.55 g. Analysis 9.2% Mg, 25.2% THF, 26.75% Ethanol. FW from analyses: 231.8. FW from thermogravimetric analysis (weight loss to pure $MgCl_2$): 220. Overall composition: $MgCl_2(EtOH)_{1.53}(THF)_{0.92}$.

The isolated material is a mixture of solvated $MgCl_2$/THF materials. The high resolution TGA scan showed 6 major episodes of weight loss over the 50° C.–250° C. temperature range, which appeared to be an overlap of the TGA of $MgCl_2$/THF and the authentic $MgCl_2(EtOH)_2(THF)_2$. Likewise, the x-ray powder pattern of the material contained peaks of $MgCl_2(THF)_2$, $MgCl_2(THF)_{1.5}$, and $MgCl_2(EtOH)_2(THF)_2$. No pure material with 1.1 $ROH/MgCl_2$ had precipitated from solution; rather, a mixture of solids with overall higher than the expected 1:1 stoichiometric ROH/$MgCl_2$ thus was obtained.

Preparation of $MgCl_2ROH)_2(THF)_2$.

$MgCl_2$ $(EtOH)_2(THF)_2$—In a 500 ml-3-neck flask equipped with a paddle stirrer and thermometer, 45 g (225 mmol) of [$MgCl_2$*1.5 THF] were slurried under a nitrogen atmosphere at 27° C. with 130-ml of THF over a water bath. Then 225 mmol of EtOH (13.2 ml) were added over 10 minutes. The slurry turned from crystalline to an opaque slush, and the internal temperature increased by 10° C. On heating the slurry to 60° C., all the solids dissolved. The solution at this point was calculated to be 175 molar in Mg at a 1:1 EtOH/Mg molar ratio. During addition of a further 225 mmol of EtOH (13.2 ml), a thick, white sludge began to precipitate. The EtOH/Mg ratio was 2.1 at this point. The mix was cooled to 25° C. and stirred for 30 minutes. A first crop solid was filtered off using a coarse frit, and was dried under a current of nitrogen at room temperature. 36 g of product was recovered. The product was identified by TGA and by wet analysis. Analysis: Formula Weight (TGA): Req: 331.2, Found: 344.9;

Req: Mg:7.34% Found 7.89%; Req. THF: 43.48% Found 46.3%; Req. EtOH 27.78% Found 23.8%.

Heat Aging of $MgCl_2(EtOH)_2(THF)_2$

A batch of undried solid was heated under a mild nitrogen purge at 70° C. Metals and ligand analysis of the dried composition gave an overall composition of 30.1% THF, 30.8% EtOH; Further drying of the samples resulted in a composition with 20.5% THE, 16.0% EtOH. TGA indicated molecular weights corresponding to the loss of weight of the compounds.

$MgCl_2(IPA)_2(TH)_2$

The compound was prepared analogously to the ethanol-containing compound described above using isopropanol as the alcohol instead of ethanol. The product was identified by TGA and by wet analysis. Analysis: Formula Weight (TGA) Req.:359.2 Found: 362.7 Req.:Mg:6.77% Found 5.5%; Req.:Cl: 19.74% Found 20.0%; Req. THF: 40.99% Found 39.8%.

Reaction of $MgCl_2$ with Dodecanol or 2-ethylhexanol

Solubility of $MgCl_2$ in THF was raised to the 1–2M range with these alcohols at 60° C. However, cooling did not result in crystalline compounds. Evaporation of the THE gave oily residues which contained both THF and the alcohols complexed with $MgCl_2$.

Reaction of $MgCl_2$ with 1,4Cyclohexanediol

On treating a 0.4M solution of $MgCl_2$ in THF with the diol at 60° C., a white precipitate formed instantly after the first few drops of diol were added. The precipitate contained a higher alcohol/Mg molar ratio than the alcohol/Mg ratio in solution. On addition of 0.25 mol diol per mol of magnesium, a precipitate with approximate composition of 0.5 diol/Mg was obtained. Precipitation continued as more diol was added. On addition of a total of 0.5 mol diol per mol Mg (or 1:1 alcohol/Mg), an enriched compound of approximate composition $(MgCl)_2(1,4-cyclohexyldiol)_1(THF)_2$ was formed. Req.:Mg 6.84%, Cl 19.95%, THF 40.5%; found Mg 6.19%, Cl 20.0%, THE 39.3%.

Reaction of $MgCl_2$ with 1,10-decanediol.

On treating 0.4 M solution of $MgCl_2$ in THE with the diol at 60° C., a white precipitate formed after the first few drops were added. The precipitate contained only minor amounts of THE.

5:1$MgCl_2TiCl_3$ EtOH/THF Solution Properties.

To a 40 liter stainless steel mix vessel were added 10.2 L THF, 10.7 mol absolute ethanol, (492 g, 625 ml), and 4.86 mol $MgCl_2$ (463 g) under nitrogen. The slurry was heated to 55° C. and stirred over night. Then was added 0.85 mol (168.9 g) $TiCl_3AA$, and the mixture was stirred for 4 hours. A solution consisting of 5:1 $MgCl_2/TiCl_3$ having a 2.2:1 $EtOH/MgCl_2$ ratio was obtained. On cooling to room temperature, white crystals precipitated which consisted of a $MgCl_2/THF/EtOH$ adduct with only minor contamination from titanium. Total evaporation of the solution gave a powdered solid which was composed of individual white and green-black particles and the individual $MgCl_2$ and $TiCl_3$ solvate compounds. No complex formation between the $TiCl_3$ and the $MgCl_2$ component had occurred.

Ball-Milling of 5:1 $MgCl_2(EtOH)_2(THF)_2/TiCl_3$ Catalyst Precursor.

To facilitate interaction of the components, the individual solids $MgCl_2(EtOH)_2(THF)_2$ (31.0 g, 93.6 mmol) and aluminum-reduced $TiCl_3$ (3.724 g, 18.72 mmol), were mixed at a 5:1 Mg/Ti ratio by ball-milling in a porcelain jar under nitrogen for 24 hours. A pink solid that refracted light under the microscope was obtained. The particle size distribution of the ball-billed particles did not change substantially after 5 minutes of stirring in a particle size analyzer. Average size was 27 μm with a span equal to 1.6. The resulting powered Mg/Ti composition was slurried in mineral oil for subsequent polymerizations (0.025 mmol Ti/g slurry).

Ball-Milling of 5:1 $MgCl_2(THF)_{1.5}/TiCl_3$ Catalyst Precursor.

To facilitate interaction of the components, the individual solids of $MgCl_2(THF)_{1.5}$ (30.5 g, 150 mmol) and aluminum reduced $TiCl_3$ (6.033 g, 30 mmol) were mixed at a 5:1 Mg/Ti molar ratio. The mixture was ball-milled in a porcelain jar under nitrogen for 24 hours. A brick-colored amorphous powder was obtained. The particle size distribution of the resulting particles decreased noticeably during 5 minutes of stirring in a particle analyzer. Average particle size decreased from 20 μm to 12 μm while the span increased from 3.1 to 3.8, reflecting a broad particle size distribution and indicating weakly connected agglomerates. The resulting powered Mg/Ti composition was slurried in mineral oil for subsequent polymerization testing (0.025 mmol Ti/g slurry).

Ethylene Polymerization Process in a Slurry Reactor.

Each laboratory scale polymerization trial was conducted as follows. To 500 ml of hexane in a 1:1 slurry polymerization autoclave were added 1.25 mmol of triethylaluminum (($C_2H_5)_3Al$) under nitrogen, followed by a mineral oil slurry of catalyst precursor containing 0.0075 mmol of Ti. The reactor was pressurized to 40 psig with hydrogen gas, then further pressurized to a total of 200 psig with ethylene. The polymerization was conducted at a temperature of 85° C. for half an hour.

TABLE I

Data From HDPE Polymerizations Using Ball-Milled Ziegler Catalyst

| Sample # | mmol Ti | Yield (g) | Activity[c] | MI (dg/min) | MFR |
|---|---|---|---|---|---|
| Control[a] | 0.0075 | 84.5 | 14,500 | 1.9 | 28 |
| 1[b] | 0.0075 | 78.1 | 13,400 | 1.6 | 28 |

[a]Precursor 5:1 $MgCl_2(THF)_{1.5}/TiCl_3$
[b]Precursor 5:1 $MgCl_2(THF)_2(EtOH)_2/TiCl_3$
[c]in gPE/mol Ti-hr-100 psi ethylene.

Thus, the data of Table I indicate that magnesium halide containing catalyst components are useful in forming active catalytic species. Moreover, the data demonstrates that the benefits of the higher solubilities of some magnesium halide components do not detrimentally affect the polymerization properties of the resulting catalysts.

As demonstrated above, embodiments of the invention provide a method of increasing the solubility of magnesium halides in solution. Embodiments also provide new catalyst precursors and methods of making such precursors. Other embodiments provide catalysts, a methods of making a catalyst, as well as a method of making a polymer. Embodiments of the invention may have one or more of the following advantages. First, increasing the solubility of the magnesium halides allows preparation of such catalysts and catalyst precursors with reduced fouling and clogging due to precipitation of the magnesium compounds in the reactors. Higher solubility of magnesium in solution also allows preparation of catalyst precursors and catalysts having higher magnesium content than previously possible. Thus, more catalyst is possible per reaction vessel, which reduces costs associated with catalyst preparation and small batch sizes. When used in polymerization reactions, these catalysts show acceptably high activity values. Thus, the catalysts provide a cost-effective alternative to existing magnesium-titanium catalysts. Moreover, some catalysts have an activity that is comparable to the activity of currently used catalysts. Thus, some catalysts described herein may be used in existing commercial processes without requiring costly re-engineering of current process parameters. The magnesium halide components described herein may also be used to form supported polymerization catalysts as disclosed in copending applications by Burkhard E. Wagner, el al., entitled "Supported Polymerization Catalyst", filed on Jul. 15, 2002, incorporated herein by reference. The precursors and catalysts may also be used to form spray-dried catalysts as disclosed in "Spray-Dried Polymerization Catalyst and Polymerization Processes Employing Same", filed on Jul. 15, 2002, incorporated herein by reference; and "Spray-Dried Polymerization Catalyst and Polymerization Processes Employing Same", filed on Jul. 15, 2002, incorporated herein by reference. These advantages are provided, in part, by the a wider range of available compositions and a more uniform distribution of magnesium in the particle. Other advantages and properties are apparent to those skilled in the art.

While the invention has been described with a limited number of embodiments, these specific embodiments are not intended to limit the scope of the invention as otherwise described and claimed herein. Moreover, variations and modifications therefrom exist. For example, various other additives, not enumerated herein, may also be used to further enhance one or more properties of the catalyst and catalyst precursor compositions and polymers made therefrom. It is understood that parameters of polymerization processes may vary, for example, in temperature, pressure, monomer concentration, polymer concentration, hydrogen partial pressure and so on. Therefore, catalysts which do not fulfill the selection criteria under one set of reaction conditions may nevertheless be used in embodiments of the invention under another set of reaction conditions. While all of the embodiments are described with reference to a single catalyst, it by no means precludes the use of two, three, four, five, or more catalysts simultaneously in a single reactor with similar or different capability for molecular weight and/or comonomer incorporation. In some embodiments, the catalysts may also include other additives or modifiers not specifically enumerated. In other embodiments, the catalysts do not include, or are substantially free of, any compounds not enumerated herein. It should be recognized that the processes described herein may be used to make polymers which also incorporate one or more additional comonomers. The incorporation of additional comonomers may result in beneficial properties which are not available to homopolymers or copolymers. While the processes are described as comprising one or more steps, it should be understood that these steps may be practiced in any order or sequence unless otherwise indicated. These steps may be combined or separated. Finally, any number disclosed herein should be construed to mean approximate, regardless of whether the word "about" or "approximate" is used in describing the number. Last but not the least, the claimed compositions are not limited to the processes described herein. They can be prepared by any suitable process. The appended claims intend to cover all such variations and modifications as falling within the scope of the invention.

What is claimed is:

1. A magnesium halide composition comprising or made from:

a) a magnesium halide;

b) a solvent suitable for an electron donor; and

C) an electron donor compound, wherein the magnesium halide is characterized by a solubility in the solvent that does not decrease as a function of the temperature up to the boiling point of the solvent and the solubility of the magnesium halide in the solvent is greater than 0.7 mol/liter.

2. The composition of claim 1 wherein (i) the magnesium halide is magnesium chloride, magnesium bromide, magnesium iodide, or combinations thereof.

(ii) the electron donor compound comprises a linear or branched alcohol having between 1 and about 25 carbon atoms.

(iii) the solvent is selected from the group consisting of alkyl esters of aliphatic and aromatic carboxylic acids, aliphatic ethers, cyclic ethers, and aliphatic ketones, (iv) the molar ratio the alcohol to magnesium halide ranges from 0.1 to less than about 1.0, and (v) the solubility of the magnesium halide in the solvent is between about 0.8 and 2.5 mol of magnesium halide per liter of solvent.

3. The composition of claim 1 wherein the composition comprises a composition of the formula

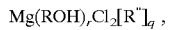

wherein ROH is an alcohol, R" is selected from the group consisting of alkyl esters of aliphatic and aromatic carboxylic acids, aliphatic ethers, cyclic ether, and aliphatic ketones, r is greater than 0 and less than 1.9, and q is greater than 0 and less than 4.

4. A composition comprising a reaction product of or mixture of the composition of claim 1 and a second component comprising a transition metal selected from the group consisting of titanium, zirconium, hafnium, vanadium, niobium, tantalum, and combinations thereof.

5. The composition of claim 4 wherein the composition comprises a composition of the formula

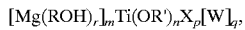

wherein
ROH comprises a linear or branched alcohol having between 1 and
about 25 carbon atoms,
R' is R'" or COR'", wherein each R'" is individually an aliphatic
hydrocarbon radical having between 1 and about 14 carbon atoms or an
aromatic hydrocarbon radical having between 1 and about 14 carbon
atoms;
X is individually Cl, Br, or I,
W is selected from the group consisting of alkyl esters of aliphatic and aromatic carboxylic acids, aliphatic ethers, cyclic ether, and aliphatic ketones,
m ranges from 0.5 to 56;
n is 0,1, or 2;
p ranges from 4 to 116;
q ranges from 2 to 85; and
r ranges from 0.1 to 1.9.

6. The reaction product of the composition of claim 4 and a cocatalyst.

7. The composition of claim 1 wherein the magnesium halide composition comprises

8. The composition of claim 1, wherein the electron donor compound comprises a substituted or unsubstituted aliphatic or aromatic alcohol having between 1 and about 25 carbon atoms.

9. The composition of claim 2 wherein the alcohol is selected from the group consisting of methanol, ethanol, propanol, isopropanol, butanol, 2-ethyl hexanol, 1-dodecanol, cyclohexanol, and di-tert-butyl phenol.

10. The composition of claim 1, wherein the solvent is selected from the group consisting of alkyl esters of aliphatic and aromatic carboxylic acids, ethers, and aliphatic ketones.

11. The composition of claim 10 wherein the alkyl esters are selected from the group consisting of methyl acetate, ethyl acetate, ethyl propionate, methyl propionate, ethyl benzoate, and combinations thereof.

12. The composition of claim 10 wherein the ethers are selected from the group consisting of diethyl ether, diisopropyl ether, and di-n-butyl ether, ethylisopropyl ether, methylbutyl ether, methylallyl ether, ethylvinyl ether, tetrahydrofuran, 2-methyl tetrahydrofuran, and combinations thereof.

13. The composition of claim 10 wherein the ketones are selected from the group consisting of acetone, methylethyl ketone, cyclohexanone, cyclopentylmethyl ketone, 3-bromo-4-heptanone, 2-chlorooyclo-pentanone, allyimethyl ketone, and combinations thereof.

14. The composition of claim 4 wherein the reaction product or mixture further comprises a second solvent selected from the group consisting of alkyl esters of aliphatic or aromatic carboxylic acids, aliphatic ethers, cyclic ethers, and aliphatic ketones.

* * * * *